United States Patent [19]
Weckström et al.

[11] Patent Number: 5,668,376
[45] Date of Patent: Sep. 16, 1997

[54] DOUBLE RADIATION SOURCE ASSEMBLY AND TRANSDUCER

[75] Inventors: Kurt Peter Weckström, Espoo; Pekka Tuomo Meriläinen; Börje Tor Rantala, both of Helsinki, all of Finland

[73] Assignee: Instrumentarium Oy, Finland

[21] Appl. No.: 605,810

[22] Filed: Feb. 23, 1996

[51] Int. Cl.⁶ .................................................. G01N 21/61
[52] U.S. Cl. ........................ 250/495.1; 250/494.1; 250/504 R; 250/343
[58] Field of Search .......................... 250/495.1, 494.1, 250/493.1, 504 R, 311, 306, 307, 343

[56] References Cited

U.S. PATENT DOCUMENTS

| | | | |
|---|---|---|---|
| 3,745,349 | 7/1973 | Liston | 250/218 |
| 4,914,720 | 4/1990 | Knodle et al. | 250/343 |
| 5,285,131 | 2/1994 | Muller et al. | 313/578 |

FOREIGN PATENT DOCUMENTS 2276975  10/1994  United Kingdom.

Primary Examiner—Jack I. Berman
Assistant Examiner—Kiet T. Nguyen
Attorney, Agent, or Firm—Andrus, Sceales, Starke & Sawall

[57] ABSTRACT

A radiation source assembly for optical transducers used for the analysis of material components of media, whereby the radiation source assembly comprises: two thermal radiation sources (1, 2), of which the first radiation source (1) is located, in relation to the second radiation source, in such a position that it emits through the second radiation source (2); a band-stop filter (10) located between the first and the second radiation sources, so that the radiation (6) emitted by the first radiation source passes through it. Both thermal radiation sources (1, 2) comprise a substrate (3, 11) made of silicon, of a silicon mixture or of a silicon compound, and a recess (53) made in the substrate, and micro-filaments (4, 5), which are fastened at their ends to the outer surface (51, 52) of the substrate, their radiation (6, 8) emitting regions being at a distance (H) from the bottom surface (54) of the recess. The stop band of the band-stop filter (10) substantially corresponds to the absorption distribution of the material component of the medium to be analyzed with the transducer.

24 Claims, 6 Drawing Sheets

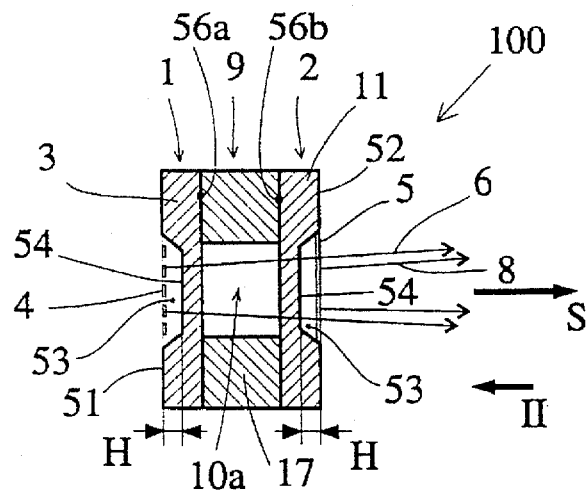
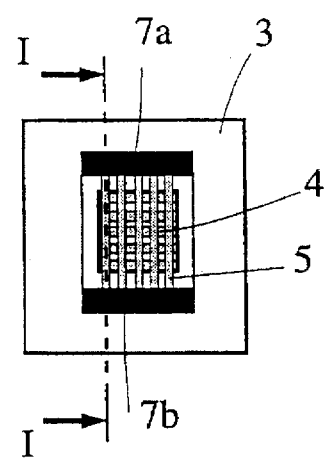
Fig. 1A  Fig. 1B
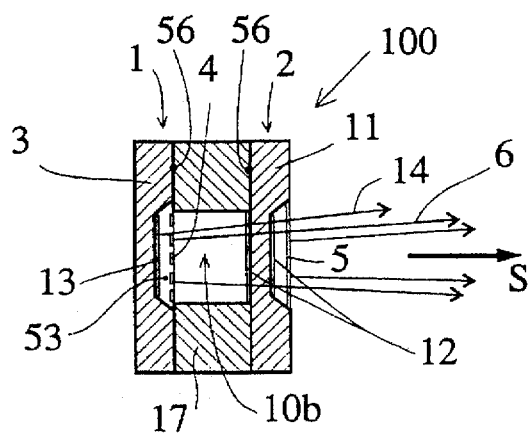
Fig. 2
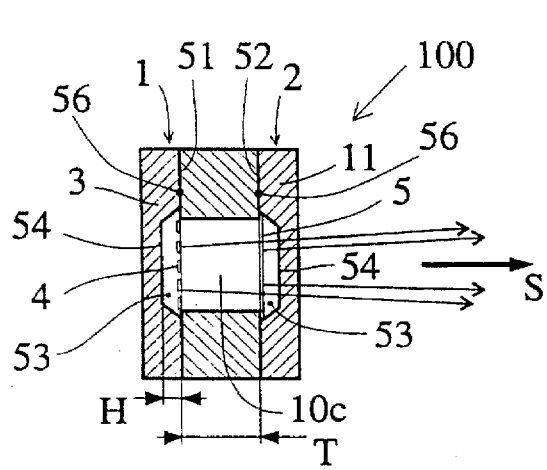
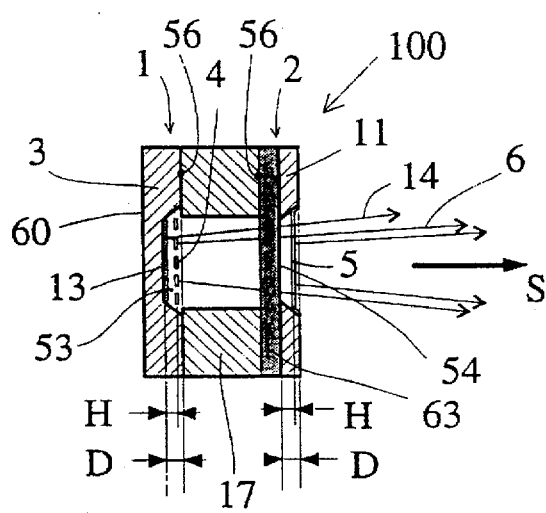
Fig. 3  Fig. 15

DOUBLE RADIATION SOURCE ASSEMBLY AND TRANSDUCER

BACKGROUND OF THE INVENTION

The invention relates to a radiation source assembly for optical transducers used for analysis of media, whereby the radiation source assembly comprises: a first and a second radiation source, of which the second radiation source is transparent for radiation emitted by the first radiation source, and of which the first radiation source is located, in relation to the second radiation source, in such a position that it emits through the second radiation source; a band-stop filter located between the first and the second radiation sources, so that the radiation emitted by the first radiation source passes through it. The invention also relates to a non-dispersive transducer utilizing such a radiation source assembly, whereby the transducer further comprises a radiation detector located to receive the radiation emitted by the first and second radiation sources. Particularly the invention relates to the analysis of gases and gaseous mixtures, although its range of use is not limited to these.

SUMMARY OF THE INVENTION

Analysis of gases based on non-dispersive infra-red absorption, such as the identification of the components of anesthetic and breathing gases and the determination of their concentrations in patient environments is currently made with transducers requiring much space. Basically there are two transducer types, transducers measuring directly in the mainstream of the patient's breathing circuit and transducers measuring in a small sidestream taken from the breathing circuit.

Sidestream transducers are generally located within a patient monitor, to which the gas sample is supplied through a thin hose. Thus the measurement is made far from the patient, which results in a delay and in the mixing of consecutive samples, which also delays the observation of changes. However, an advantage is the minor importance of the transducer size and the short distance between the whole measurement electronics and the transducer. Corrections to the transducer signal are then easily made, and therefore the concentration readings are usually very accurate and reliable but, consequently, they are obtained with a delay. The transport of the gas samples to the monitor can take a few seconds, and also the rise time of the signal can be longer due to the above mentioned mixing. It is mainly due to this disadvantage that the mainstream transducer is becoming more common, particularly in applications where speed is important.

Mainstream transducers, on the other hand, are connected to the mainstream of the patient's breathing by a special connector. A mainstream transducer of this kind is described e.g. in the publication U.S. Pat. No. 4,914,720. The transducer comprises a measurement chamber or connecting tube, which forms a section of the mainstream channel and which has two opposite windows. The transducer itself is located outside the windows, so that the transducer's infra-red source is directed from the outside towards one of these windows and directs the radiation through the mainstream channel towards the second window, on the outside of outside of which is placed at least one detector with its narrow band filter. However, typically two detectors are used, of which one measures carbon dioxide through a narrow band filter, and a second detector makes reference measurements through a narrow band filter operating on another wave-length band in order to correct e.g. disturbances occurring in the radiation intensity. The electrical signals from this transducer are supplied via electrical lines to a device which calculates the measurement result. A disadvantage of transducers of this type is the signal's sensitivity to the erroneous absorption caused by water and mucus, which accumulate on the windows of the measurement chamber. By heating the windows of the measurement chamber it is possible to avoid the condensation of water, but this practice can not reliably compensate for the shading effect of the mucus. The reason for this is that the reference detector will see the mount of mucus differently than the proper measurement detector, because the band of the narrow band filter of the reference detector and the band of the narrow band filter of the proper measurement detector are on different wave-length ranges, so that the radiation which passed through the mucus will pass these through filters in different ways. Further the measurement and reference beams located e.g. in parallel have a different geometric distribution in the measurement chamber and this can cause differences in the measurement and reference signals.

Another transducer like the mainstream transducer described above to be placed in the mainstream is described in the publication HEWLETT-PACKARD JOURNAL, September 1981, pages 3–5,: R. J. Solomon—"A Realiable, Accurate $CO_2$ Analyzer for Medical Use". In the described transducer construction the measurement accuracy is increased, and particularly the drift of the measurement value is reduced by modulating the infra-red radiation passing through the measurement chamber with a rotating filter disk, in which the filters comprise closed cells containing exactly known gaseous mixtures. One cell contains carbon dioxide, because the transducer measures carbon dioxide. In a solution of this kind the measurement geometry and reference geometry are approximately equal, and thanks to the optical gas filter also the measurement and reference wave-length bands are equal, as is described in the publication. However, a transducer of this kind is very complicated, expensive and very sensitive to blows etc. Further there can occur wear of the bearings of the filter disk, which increases the unreliability and the service costs.

The use of an optical gas filter is known e.g. from the publication U.S. Pat. No. 3,745,349. This transducer contains two infra-red sources, of which one radiates through the other, whereby the radiation from both infra-red sources have exactly the same optical path. Between the infra-red sources there is a filter, which is based on the optical absorption of gas, and which provides a very narrow absorption band at the center of the somewhat wider absorption band of the gas to be measured. The infra-red sources are used alternately, so that a detector placed on the opposite side of the measurement chamber as seen from the infra-red sources receives alternately the proper measurement signal and a reference signal, which now have propagated the same path and see the water and mucus approximately in the same way because of the approximately same wave-length range. This proposed structure eliminates a major part of the disadvantages discussed above. However, the structure of the publication U.S. Pat. No. 3,745,349 has such disadvantages that the proposed structure has not found practical use. If conventional long-lasting miniature incandescent lamps with a burning time of a few thousand or tens of thousand hours are used as infra-red sources in the transducer, then due to their slowness it is possible to realize only a very slow alternation of the radiation sources, i.e. a slow modulation. Then the measurement speed achievable with the transducer is not sufficient. On the other hand, if the filaments are made thinner and smaller to an extent that a sufficiently rapid modulation is possible, the filaments will burn off very fast, so that the transducer has a very low functional value. Errors are also caused by the fact that the filaments have a rather large area in the radiation's propagation direction, so that the proper measurement radiation source shades the reference radiation source and causes different paths for the beams at the measurement chamber. Further errors can be caused by the fact that the wave-length distribution of the reference beam is substantially narrower than the wave-length distribution of the measurement beam which is passed through the measurement chamber. Moreover, the transducer realized in the way described is so bulky that it can be used only as a sidestream transducer. Therefore the transducer presented in the publication has a fixed sample chamber, and thus it is not suited for a mainstream transducer, for instance.

Thus the object of the invention is to provide a radiation source assembly, particularly an assembly emitting infra-red radiation, which is suited to be used as a radiation source in a transducer for the analysis of gas components by a non-dispersive infra-red absorption method, and which comprises a radiation source emitting a measurement beam and a radiation source emitting a reference beam. The second object of the invention is such a radiation source assembly, where the output paths of the measurement beam and the reference beam are as accurately identical as possible, whereby their paths in the measurement chamber are made exactly the same. The third objective of the invention is such a radiation source assembly, where the wave-length distribution of the reference beam corresponds as exactly as possible to the wave-length distribution of the measurement beam after the measurement chamber, whereby the effect of any impurities in the measurement chamber can be eliminated regardless of their nature. The fourth object of the invention is such a radiation source assembly, where the thermal time constant of both radiation sources is so short that it is possible to operate both radiation sources alternately with a pulse current, i.e. to have a pulsed modulation of both sources at a so high frequency that a reliable and accurate measurement result can be obtained from a gaseous mixture changing at least in the breathing rhythm. Thus the modulation frequency must be at least a multiple of the breathing frequency. The fifth object of the invention is a radiation source assembly with a very long life time, and thus radiation sources having a particularly a long life-time and a long time between failures. An object is also to provide a transducer, which utilizes such a radiation source assembly, which is sufficiently small to be used as a mainstream transducer, which contains no moving parts, and which is cheap to manufacture, reliable, and has a long life-time. The aim is particularly to provide a transducer with a very small size and comprising a combination of a radiation source assembly and a detector.

The above described disadvantages can be eliminated, and the above defined objects can be achieved with a radiation source assembly according to the invention, which is characterized in the claims, and with a transducer according to the invention, which is characterized in.

The most important advantage of the double infra-red radiation source, i.e. the radiation source assembly according to the invention, is that it can be made very small, fast, long-lasting and reliable. So called micro-mechanics is used in the manufacturing of a single radiation source in order to achieve this, whereby the dimensions of the radiation source can be of the order from a few tens or hundreds micrometers to a few millimeters, and the other dimensions of the thermally radiating parts of the radiation source, i.e. the micro-filaments, can be of the order of micrometers or possible even less. The time constant of the radiation source can be made small due to the small thermal mass obtained in this way and due to the fact that the micro-filaments are at a suitable distance from their substrate. Due to this very small size of the micro-filaments the forces acting on them are weak, whereby the probability of having a hot micro-filament breaking is drastically reduced in comparison to a common large-size filament. The life-time can be increased even more by a material choice according to the invention. According to the invention the combination of the two radiation sources is made by attaching these radiation sources on both sides of the gas cavity forming the optical gas filter. As an absorbing medium in the gas filter we use exactly that medium, such as a gas, which is to be measured with the transducer, whereby we obtain an optimal wave-length distribution for the reference beam. Even if the gas to be measured is functioning best as the medium, it is obvious that it would also be possible to use as the medium of the filter such solid or liquid material or other band-stop filter, which has an absorption band or stop band which is as close as possible to that of the gas to be measured. The stop band can be of the absorptive type, but also of the reflective type, as is common in filters based on the interference of radiation. A very compact double radiation source is obtained, when further the substrates of the radiation sources, or at least the substrate of the radiation source providing the measurement beam, are transparent for the wave-lengths used in the measurement, and when required this radiation source can be easily mounted in a TO-5 package, well-known e.g. in the semiconductor industry, or in any other corresponding package. The double source can be combined to be a mainstream transducer, for instance, by adding, for the gas to be examined a measurement distance in from of the radiation source assembly, and for the radiation a detector provided with a narrow-band filter corresponding to the wave-length distribution of the absorption band of the medium under examination.

BRIEF DESCRIPTION OF THE DRAWINGS

Below the invention is described in detail with reference to the enclosed figures.

FIG. 1A shows the double infra-red source according to the invention in a longitudinal section in the main propagation direction of the radiation along the plane I—I FIG. 1B.

FIG. 1B shows the double infra-red source in a front view in the radiation output direction, i.e. seen in the direction II of FIG. 1A.

FIGS. 2 to 5 show a second, a third, a fourth and a fifth alternative embodiment of the double infra-red source according to the invention in a longitudinal section in the main propagation direction of the radiation, in the same view as FIG. 1A.

FIG. 15 shows a further embodiment of the double infra-red source according to the invention in a longitudinal section in the main propagation direction of the radiation, in the same view as FIGS. 1A and 2 to 5.

DETAILED DESCRIPTION OF THE PREFERRED EMBODIMENT

Figure 7:
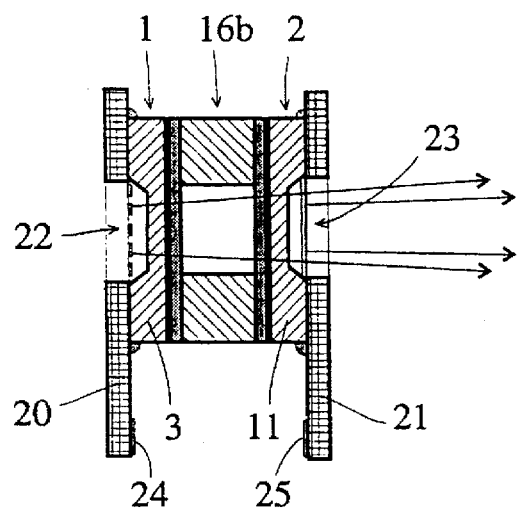
FIGS. 7 and 8 show a sixth and seventh alternative embodiment of the double infra-red source according to the invention in a longitudinal section in the main propagation direction of the radiation, in the same view as FIGS. 1A and 2 to 5, whereby the embodiments utilize a separate optical gas filter and comprise electrical terminals.
Figure 13:
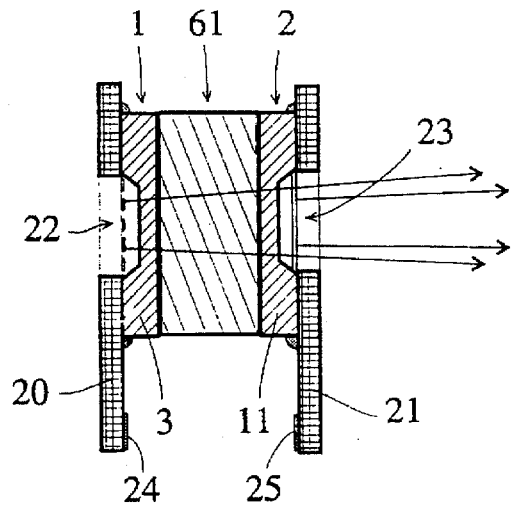
FIGS. 13 and 14 show an eighth and ninth embodiment of the double infra-red source according to the invention, which in other respects correspond to the embodiment of FIG. 7, except that instead of the gas filter there is a solid mass filter and an interference filter, respectively.
Figure 8:
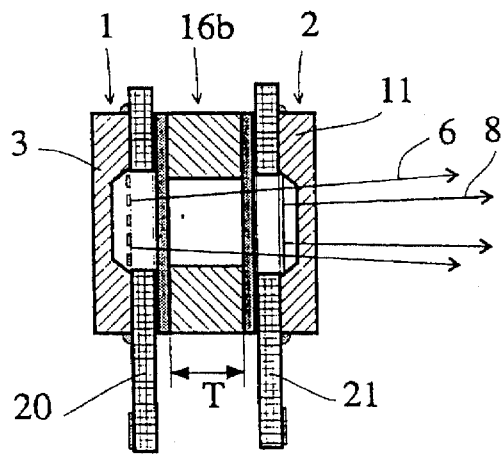
Figure 14:
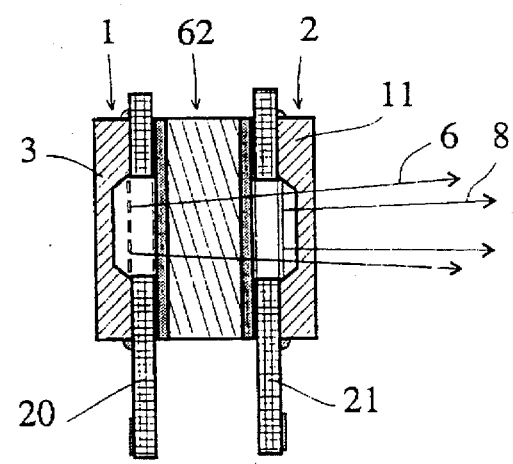

The FIGS. 1A and 2 to 5 show in a longitudinal section some construction details of the double infra-red source according to the invention, i.e. the radiation source assembly 100. FIG. 1B shows the source of FIG. 1A seen from the front in that direction, in which the radiations 6, 8 leave the assembly 100. The radiation source assemblies of the other FIGS. 2 to 5 are almost similar, as seen from the front. This main propagation direction of the radiation is marked by the numeral S, and it is preferably perpendicular to the planes of the thermal radiation sources 1 and 2 emitting radiation due to heating. The first radiation source 1 and the second radiation source 2 are placed on the same line, so that the radiation 6 emitted by the first radiation source 1 passes through the second radiation source 2, whereby both emitted radiations 6 and 8 together form a radiation beam having, which has the main direction S and which is utilized in the transducer described below. The radiation source assembly 100 further comprises a filter chamber 10a, 10b, 10c, 10d oar 10e, or a filter chamber 16a or 16b of an alternative type, as shown in FIGS. 7 and 8, or a mass filter 61, as shown in FIG. 13, or an interference filter 62, as shown in FIG. 14. A filter chamber 10a–e, 16a–b, and correspondingly a filter 61 or 62 is placed between the first and second radiation sources 1 and 2, so that the radiation 6 emitted by the first radiation source passes through the filter, whereby there occurs a desired absorption of the radiation, due to the gas or other medium present in the chamber or due to the filter medium or due to the interference coating.

In the presented cases both radiation sources 1, 2 are made according to the invention with the so called silicon micro-tooling technique. The micro-tooling technique has become common in recent years, and made it possible to fabricate different micro-mechanical components having details with dimensions of the order of micrometers and main dimensions perhaps of the order of millimeters. This technique is related to the methods used in the manufacturing of semiconductors, and in this method different forms are made in a silicon crystal directly by etching, e.g. with the aid of different protecting masks, or by growing different thin films on the surface of the silicon crystal by vaporizing, sputtering, printing or another technique known from the manufacturing of integrated circuits, the so called thin-film technology. A radiation source made in this technology typically comprises a substrate 3, 11 with an outer surface 51, 52. Micro-filaments 4, 5 are then gown or printed with a suitable coating technique on this outer surface, or on another surface obtained with any suitable technique and located at another place or having another shape, and thus the filaments are flat and in the plane of the substrate's outer surface. In the figures the micro-filaments are straight, but it is obvious that they can be made in another form when required, for instance in a wave form. The micro-filaments can be printed or gown directly in their final form, or they can be shaped for instance by etching a coating first made in another form. As shown in FIG. 1B, the micro-filament array of one radiation source comprises a plurality of individual filaments connected in parallel, so that they form a flat emitting region, which emits mainly in the direction S perpendicular to this emitting region, i.e. to the micro-filaments 4, 5 and thus also perpendicular to the outer surfaces 51 and 52 of the substrates. In practice there are generally substantially more filaments than the five shown in the figure. Usually the number of individual micro-filaments in the micro-filament array is of the order 20 to 50. According to the invention a recess 53 is etched in the substrate in the region of the micro-filaments 4, 5, i.e. in the region which emits the radiation. Thus the micro-filaments are at a distance H from the bottom surface 54 of the recess 53, which provides the micro-filaments with a small thermal capacity and thus a short thermal time constant. The volume of an individual micro-filament 4, 5 is at most about 200,000 $\mu m^3$, preferably at most about 50,000 $\mu m^3$, and typically of the order 2,000 to 20,000 $\mu m^3$, whereby the thermal time constant of the micro-filament is at most about 50 ms, preferably at most about 10 ms, and typically of the order 0.5 to 5 milliseconds. Thus a single micro-filament has a typical thickness of the order 0.5 to 5 $\mu m$, a width of the order 5 to 100 $\mu m$, and a length of the order 50 $\mu m$ to 3 mm. The distance H from the bottom 54 of the recess 53 to the micro-filaments 4, 5 is generally of the order 10 to 1000 $\mu m$, and typically of the order 5 to 300 $\mu m$. A suitable distance H improves the cooling of the filaments 4, 5 when the substrate 3, 11 acts as a heat conductor, however, without delaying the rate of rise of the filament's heating. A too long distance H decreases the rate of rise, but on the other hand a too short distance H could lead to a too low temperature of the micro-filament region, whereby the amount of light obtained from the radiation source will decrease. A too short distance H could also cause the filaments to adhere to the bottom 54 of the recess 53. In the embodiments of the figures the micro-filaments are thus almost in the plane of the substrate's outer surface 51, 52, or at such a distance from the plane which corresponds to the thickness of any electrically isolating coating made on the substrate and/or to the thickness of the micro-filament itself, which distance can not be seen in the figures. If desired, the micro-filaments can be placed substantially deeper in the recess, as shown in FIG. 15, or possibly more outwards from the substrate's outer surface 51, 52 in a way not shown in the figures, if only the distance H between the micro-filament and the bottom of the recess has a magnitude described above. However, this requires that the topography and/or the level of the substrate is changed by any of the above mentioned methods of the thin-film technology, i.e. by etching and/or by coating. The micro-filaments can also be made undulating, e.g. in the direction of the distance H, or in some other shape, and further it is possible to place the micro-filaments at different depths in the same radiation source.

The technique to make the infra-red source 1, 2 manufactured with such a silicon micro-tooling technique is detailed in the Finish patent publication FI-931570. The infra-red source comprises a body or substrate 3, 11 made of silicon, and a plurality of thin micro-filaments 4, 5. According to the mentioned publication these filaments are polycrystalline silicon, which is doped to become conducting and protected by silicon nitride, but they can as well be another material suitable for the thin film technique, such as metal, for instance tungsten, as is described in the article "Hot-filament microlamps now feasible" (Laser Focus World, December 1992, pages 26 to 31). The silicon is etched away under the filaments, so that the filaments become self-supporting and attached at their ends to the outer surface 51, 52 of the substrate 3, 11. The second infra-red source 2 on top is made in the same way as the first infra-red source 1, although it is turned as shown in the picture so that the filaments 5 are perpendicular to the filaments 4 of the source 1, the planes of the filaments being parallel. However, this is not a prerequisite, but the idea is to have as much as possible of the radiation 6 of the source 1 to pass through the filament region of the source 2. The filaments 4, 5 of the infra-red source are electrically connected to metallized electrodes 7a and 8b, which act as terminal electrodes to the rest of the electronics. If the filaments 5 of the second source 2 are silicon, they are, as far as is known, transparent for infra-red radiation at room temperature. This improves the passage of the radiation 6 of the first radiation source, because the radiation sources 1 and 2 are alternately on. In any case the second radiation source 2 must not shade the radiation 6 emitted by the first radiation source 1 but for a rather small part, i.e. the second radiation source must be clearly or substantially transparent for the radiation 6, regardless of whether its filaments themselves are transparent for the radiation or not. Also the substrate of the second radiation source 2 must not substantially prevent the passage of the radiation 6 from the first radiation source. If necessary, the filament material could be coated with a separate film preventing oxidization or vaporization, or with a film improving the emissivity of the filament, or with both. Such films can be formed of silicon nitride, silicon carbide, and of the oxides of different metals. When the emission factor of the micro-filament is increased in this way its temperature can be kept low, which increases the life-time. The life-time is also increased by the fact that the micro-filament is made of such material or coated with such material, which has a vapor pressure as low as possible at the emission temperature. A low emission temperature also lowers the vapor pressure, which further increases the life-time. The substrate 3, 11, can be made of preferably such relatively pure silicon, which is commonly used for the manufacturing of semiconductors, because it is a relatively cheap material, and the etching of it and other treatment is per se a known technique, and because such sufficiently pure silicon is transparent for infra-red radiation in room temperature. Without any particular measures the radiation 6 emitted by the first radiation source 1 can then pass without any impediment through the substrate 11 of the second radiation source 2, particularly in the region of the recess 53 in the substrate 11. It is of course possible to use doped silicon or silicon compounds as the material of the substrate, but due to the mount of doping, the type of the doping material and the type of the compound, this may result in another structure described below, due to the fact that the substrate may be insufficiently transparent for the radiation which is used. The substrate must be either insulating material or it has to be coated with an insulating material, on which the micro-filaments are gown, so that suitable electrical terminals can be made on the substrate, as was described above.

If the substrate 11 of the second radiation source 2 is of a material, which is non-transparent for the used radiation, such as the infra-red radiation, then the recess 53 must be replaced by a bore through the substrate, so that the radiation 6 emitted by the first radiation source can pass through the second radiation source 2. Then a bottom piece 63 forming the bottom 54 must be placed behind the substrate 11 of the second radiation source, and if required also behind the substrate 3 of the first radiation source, seen from the micro-filaments 4, 5, whereby the correct distance H is obtained between the bottom thus formed and the micro-filaments, and thus the desired temperature and rise time of the micro-filaments is obtained in the way described above. The material of the bottom piece 63 shown in FIG. 15 must of course be transparent to the radiation in use, such as glass, sapphire, quartz, silicon nitride or calcium fluoride.

Both radiation sources 1, 2 are preferably arranged to emit with substantially the same wave-length distribution, i.e. the micro-filaments 4, 5 are arranged to glow at the same temperature. It is also preferable that the emitting areas of both radiation sources seen from the detector are at least approximately equally large at the same wave-lengths. The distribution in the cross-section of the propagation direction of the radiation 6 emitted by such a radiation source 1, seen from the front, is substantially equal to the distribution in the cross-section of the radiation 8 emitted by the infra-red source 2, which is essential particularly in a mainstream transducer, so that dirt or any other obstacles in the measurement path, i.e. in the radiation propagation path affects the radiation from both sources in the same way. Then the signal error can be compensated for, and it will not interfere with the measurement.

In the FIG. 1A a glass plate 17 provided with a hole is hermetically attached, e.g. by electrostatic bonding, between the infra-red sources 1 and 2. The hole is as large as or larger than the area defined by the filaments 4 or 5. The chamber 10a thus formed is filled with gas, which absorbs as accurately as possible at the same wave-length as the gas to be analyzed by the transducer using the radiation source assembly. According to the invention this filter chamber 10a, and of course also the other filter chambers 10b–10e and 16a, 16b, preferably contains exactly that gas or more generally that medium, which is to be measured by the transducer. If the transducer, in which the radiation source assembly 100 according to the invention is placed, measures for example carbon dioxide, then also carbon dioxide is enclosed in the chamber. In this way an optical gas filter 10, 16 is obtained. The concentration of the gas enclosed in the filter chamber 10a–e, 16a–b is selected so that as much as possible of the absorption of the radiation 6 from the first infra-red source 1 takes place in the filter chamber, whereby there is substantially no absorption of the first radiation 6 in the measurement chamber containing the actual gas, gaseous mixture or corresponding medium to be analyzed. The first radiation 6 which got through will then not substantially react with said gas, so that the first infra-red source 1 can act as a reference. The radiation 8 emitted by the second infra-red source is compared with the radiation emitted by the infra-red source 1, whereby it is easy to compensate for absorption caused by anything else but the gas to be measured.

Figure 9:
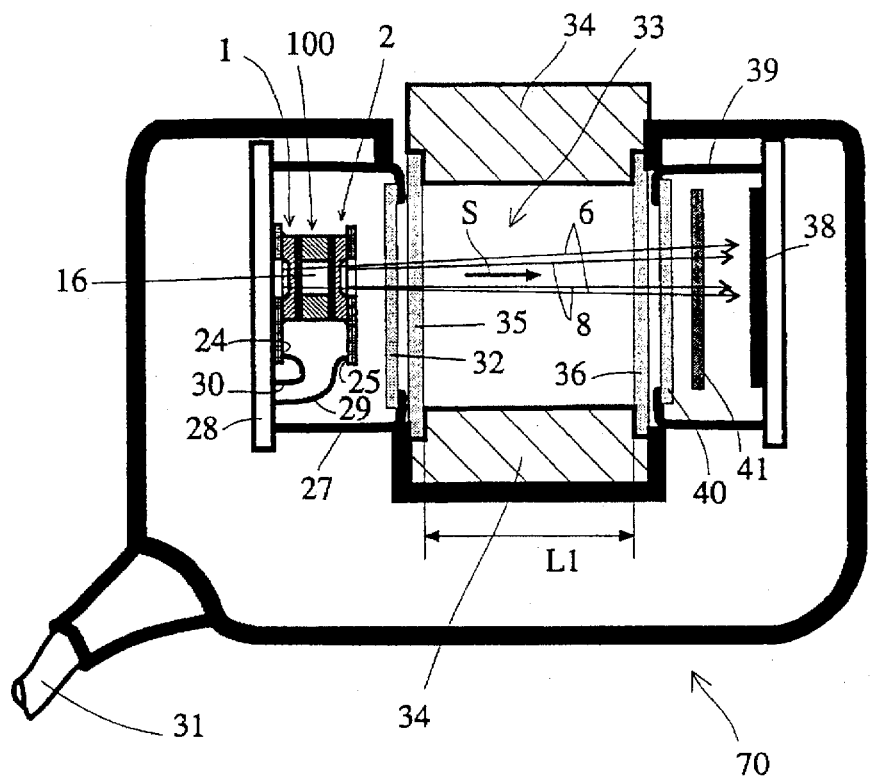
FIG. 9 shows an embodiment of the transducer according to the invention, in which the modulated infra-red radiation from the radiation source assembly passes once through the sample gas volume, and where the absorbed radiation is detected with a detector provided with a narrow-band filter.
Figure 10:
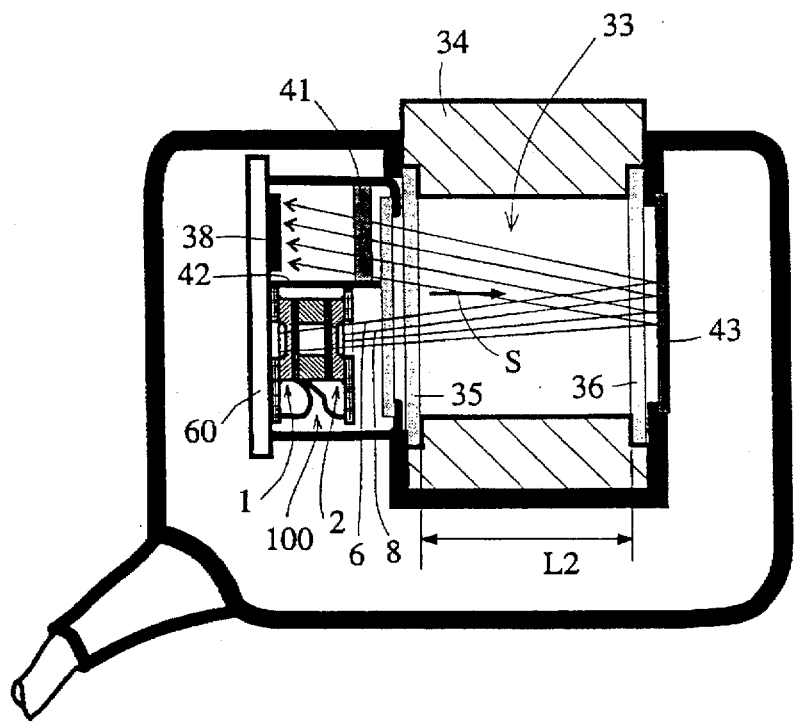
FIG. 10 shows another embodiment of the transducer according to the invention, in which the radiation source assembly and the detector provided with a narrow-band filter to detect the absorbed radiation are located on the same side of the sample gas volume, and in which the modulated infra-red radiation is reflected in a mirror, so that it passes two times through the sample gas.

The dimensions of the double infra-red sources contained in the transducers shown in FIGS. 1A and 2 to 8 as well as in FIGS. 9 and 10 are typically a few millimeters. In a preferred embodiment the area covered by the filaments 4 or 5 is about 0.2 to 5 mm$^2$, and the size of the filter chamber in a direction transverse to the main propagation direction of the radiation is at least equal to the area covered by the filaments. The thickness T of the filter chamber 10a–e and 16a–b in the propagation direction S of the radiation depends on the gas and on its concentration, but typically it is 0.5 to 5 mm, preferably of the order 1 to 2 mm.

According to FIG. 1A the filaments 4 and 5 of both infra-red sources 1 and 2 are outside the filter chamber 10a, and thus directed away from each other.

FIG. 2 shows a solution in which the micro-filaments 4 of the first radiation source 1 are within the filter chamber 10b, and thus the emitting parts of both sources are directed in the same main propagation direction S of the radiation. The solution is possible, if the gas in the filter chamber can withstand the heat (about 500° to 800° C.) without decomposing. An advantage is that the losses of the first radiation 6 decrease when the surface reflections caused by the substrate 3 of the first radiation source 1 are eliminated, and further the filaments are well protected. However, the surface reflections caused by the silicon substrate 11 of the second radiation source 2 are still present. They can be substantially reduced by coating both sides of the substrate 11, i.e. the bottom of the recess 53 and the surface region of the substrate opposite the recess, with an anti-reflective film 12 based on interference and known per se, at least on that area through which the radiation passes. Further it is possible to coat the region below the micro-filaments 4 of the first radiation source 1, i.e. the bottom 54 of the recess 53, with a reflective film 13, e.g. aluminum, whereby a part 14 of the radiation by being reflected can reach the correct direction S. In this way the source's 1 relative share of the whole radiation increases, even if at the same time it is possible that a small part of the source's 2 radiation is also reflected in the same mirror 13. The reflective film 13 can of course also be placed on the back surface 60 of the substrate 3 of the radiation source 1.

Basically the micro-filaments 4 and 5 of both radiation sources 1 and 2 could be within the filter chamber 10c, as in FIG. 3. In this way they are well protected against mechanical damage and also against the oxidizing action of the surrounding air. Also in this case the peripheral walls 17, which define the chamber in the direction perpendicular to the main path S of the radiation in the chamber 10c, as well as in the chambers 10b and 10a of the above described embodiments, are made of any suitable material, such as glass, ceramics or metal, and connected 56 hermetically to the substrates 3, 11 of both radiation sources. The substrates of the radiation sources define the chambers 10a–10c in the direction of the radiation path, and thus in the easiest case the substrates are of a material which is transparent for the radiation in use. This requirement is mandatory in the embodiment of FIG. 1A, but not in the embodiments of FIGS. 2 and 3 regarding the first radiation source 1, which is obvious also owing to the mirror coating 13 described above.

Figure 4:
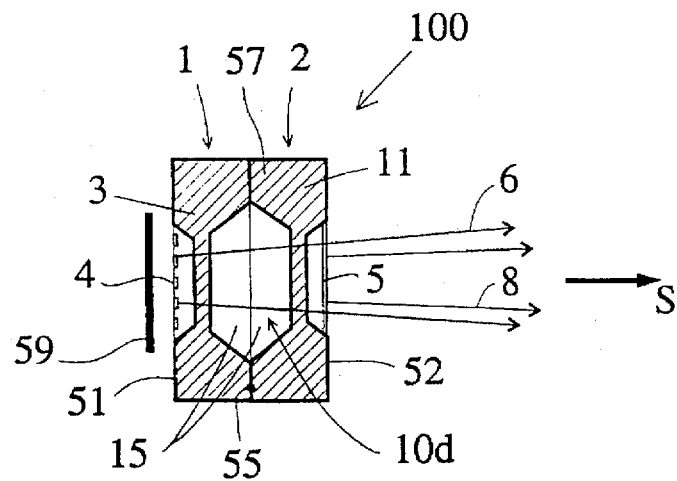
Figure 5:
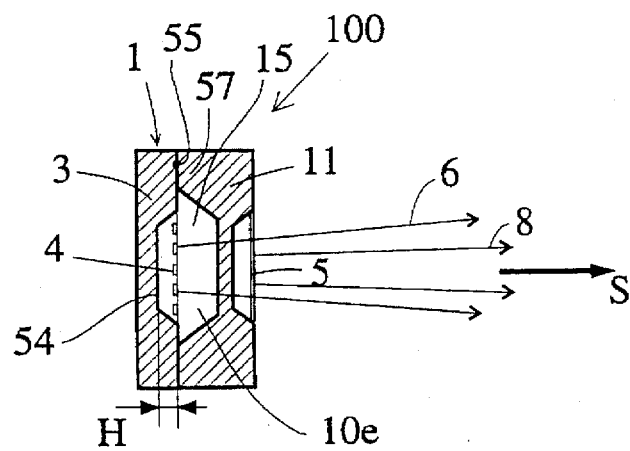

FIG. 4 shows a solution, in which the filter chamber 10d is not made in a glass body, but a part of the back-side of the silicon substrates 3, 11 of the infra-red sources 1 and 2, seen from the side of the micro-filaments, are etched to form a sufficiently deep hollow 15. When the substrates are placed against each other so that the filaments 4, 5 point away from each other, the substrates define a filter chamber 10d between them. A desired gas can be enclosed in the chamber because it is also easy to attach 55 silicon hermetically to silicon. In order to provide the filter chamber 10e it suffices to make another hollow 15 in the other substrate 11, if the etching is sufficiently deep, as in FIG. 5. Then it is possible to move e.g. the filaments 4 of the first radiation source 1 into the chamber 10e, if the enclosed gas permits this. In both these cases the walls defining the chamber 10d–e, both the peripheral wall 57 transverse to the radiation propagation direction S and the walls in the radiation propagation direction, are made of the substrate materials of the radiation sources 1, 2. In the embodiment of FIG. 4 there is further a separate mirror surface 59 behind the first radiation source 1, seen against the main propagation direction S of the radiation, this surface reflecting the radiation 6 emitted by the first radiation source towards its main propagation direction, exactly as the mirror coating 13 of the embodiment in FIG. 2.

Figures 6A, 6B:
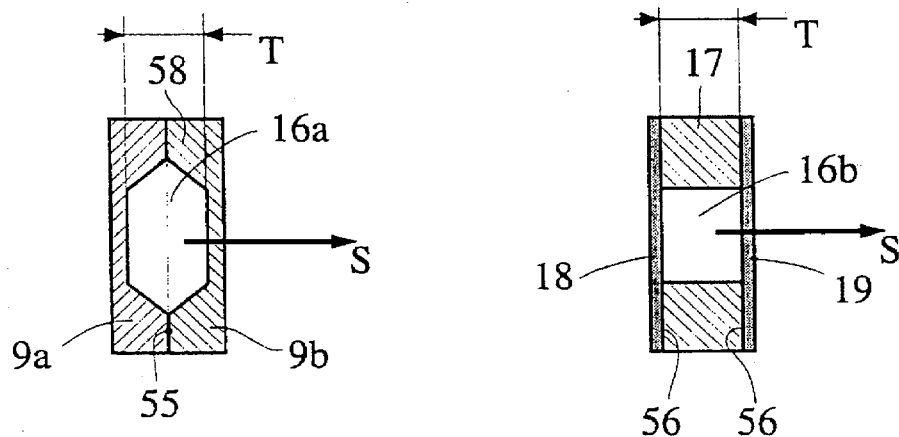
FIG. 6A shows an embodiment of a separate optical gas filter in a longitudinal section in the main propagation direction of the radiation, in the same view as FIGS. 1A and 2 to 5.
FIG. 6B shows a second embodiment of a separate optical gas filter in a longitudinal section, in the same view as FIG. 6A.

Sometimes it may be preferable to enclose the gas of the optical gas filter 10, 16 in a container which is separated from the radiation sources 1, 2. FIG. 6 shows two ways to construct a container or filter chamber. In FIG. 6A the filter chamber 16a is formed between the silicon plates 9a, 9b with deep etchings, in the same way as in FIG. 4. The silicon plates 9a, 9b define the chamber both in the propagation direction S of the beams and in the direction transverse to it by the peripheral wall 58. In FIG. 6B the filter chamber comprises a body, which forms the peripheral wall 17 provided with a hole, and two windows 18 and 19 transparent for infra-red radiation. The body can be of glass, ceramics, silicon or metal, and the windows 18, 19 can be of silicon or some other suitable thin material transparent for infra-red radiation, such as glass, sapphire, silicon nitride or calcium fluoride. In this case the anti-reflection film may be unnecessary due to the lower refractive index of the window material. The windows 18 and 19 can be attached 56 hermetically to the peripheral wall 17 by gluing or by any other suitable bonding method.

The electrical connections of the radiation sources 1 and 2, as well as the assembly of the double infra-red source, will be easier using a separate optical gas filter 16a, 16b. FIG. 7 shows one such solution. The substrates 3 and 11 of the infra-red sources 1 and 2 are each attached to an electronic circuit board 20 and 21, respectively, by soldering or a with conductive glue. The circuit board has a hole 22 and 23 at the region of the filaments and metallizations 24 and 25 for electrical connections. The filter chamber 10a or 10d could also in this case be bonded to the substrate 3 and 11 of the infra-red sources, as in FIG. 4, but a separate chamber 16 could be used as well and it could be attached by gluing as in FIG. 7, particularly when in the case shown in the figure the gluing has not to be hermetic. The hole 22 and 23 in the circuit board protects the filaments against mechanical contact when the infra-red sources are turned as shown in FIG. 7. In the solution of the FIG. 8 the filaments are even better protected, when the circuit boards 20 and 21 are turned to face each other. Then there will not occur reflections, possibly caused by the substrate 3 of the infra-red source 1.

In order to filter the radiation 6 of the first radiation source 1 before it passes through the second radiation source 2 it is also possible to use a filter chamber of the type described above as a band-stop filter which is filled with a liquid medium, or a filter body 61 of a solid medium as in FIG. 13, or an interference filter 62 based on radiation reflection as in FIG. 14. However, regardless of the band-stop filter type it is essential that its stop band corresponds as exactly as possible to the absorption distribution, which the material component to be analyzed has on that wave-length band which is used in the analysis.

FIG. 9 shows a transducer 70 according to the invention designed as an infra-red analyzer, of which a double infra-red source 100 of the type described above is one part. Here the double infra-red source 100 is according to the FIG. 7, and it is attached to the bottom plate 28 of a transistor casing 27, so that the first radiation source 1 is against the bottom plate and the second radiation source 2 is directed outwards from the bottom plate. Through the connection metallizations 24 and 25 and by connection wire pairs 29 and 30 the radiation source assembly 100 is connected to controlling electronics not shown in the figures, and to a power supply by the connecting wire 31. The transistor casing 27 can have a window 32, which is transparent for infra-red radiation and through which both radiations 6 and 8 emerge almost or exactly identically in the direction S, but the window is not essential for the operation, as is not the casing. The gas or gaseous mixture to be analyzed is in the space 33, and normally it is a measurement chamber enclosed by the walls 34 and two windows 35 and 36 transparent for infra-red radiation. The gas in the space 33 can flow as in a mainstream transducer, in which the walls 34 and the windows 35 and 36 represent the detachable connector of a breathing pipe, but regarding the operation it is unimportant whether the gas is flowing or stationary. The reference radiation 6 and the measurement radiation 8 leaving the double infra-red source 100 emerge as alternately modulated radiations in the direction S and pass through the gas in the space of the measurement chamber 33, so that the gas absorbs from the measurement beam 8 a part corresponding to its partial pressure, and possibly an insignificant part from the reference beam 6. If the measurement concerns carbon dioxide, and the optical gas filter 16 contains carbon dioxide, then the measurement radiation 8 encounters a higher absorption than the reference radiation, because the largest part of the carbon dioxide absorption took place already in the gas filter 16. It is possible to influence to some degree the linearity of the gas measurement with the length T of the filter chamber 16 or the carbon dioxide content of the gas in the filter chamber 16, although this fact is of a lesser importance as the measurement signals are anyway processed digitally.

According to FIG. 9 the detector 38 is on the other side of the gas 33 to be measured and it detects the radiations 6 and 8. Since the infra-red sources 1 and 2 are alternately on, one detector is sufficient to detect both signals. The detector 38 is preferably lead selenide, but any other sufficiently fast infra-red detector is also possible. The detector 38 according to FIG. 9 is within the transistor casing 39, and the casing is provided with a window 40 transparent for infra-red radiation, but this is not necessary for the operation. In front of the detector there is a narrow-band filter 41, which is transparent for wave-length band only a slightly wider than the band in which the gas or medium to be analyzed has its absorption state (for carbon dioxide 4.26 µm). The passband of the narrow-band filter extends so far on both sides of the absorption maximum that a sufficient mount of reference radiation is supplied to the detector. This filter 41 could also act as a window instead of the window 40. Thus both the reference radiation and the measurement radiation 6 and 8 pass through the gas 33 to be measured in a geometrically equal way, and also on the same band of the specimen, because they are measured through the same narrow-band filter 41 and with the same detector. This is essential regarding the measurement accuracy, because then there is no effect on the measurement radiation and the reference radiation if the windows 35 and 36 get dirty, not even if they absorb the radiation differently on different wave-lengths. In a mainstream transducer the use of this kind of a solution is required by reliability and high measurement accuracy. Usually the transducer further contains a pre-amplifier for the detector 38 and heating of the windows 35 and 36, which are not shown in the figures. All control and measurement signals are supplied through the connecting line 31 to a monitor not shown in the figures, where the actual measurement electronics, the calculation algorithms and the display are located.

FIG. 10 shows an alternative solution for the transducer realized as an infra-red analyzer. In this solution the double infra-red source 100 and the detector 38 and the narrow-band filter 41 are on the same side of the gas 33 to be measured. In the embodiment of the figure the radiation source assembly 100 and the detector 38 are placed in parallel in the direction transverse to the radiation direction, but this placement is not mandatory. An optically black partition 42 prevents the radiation 6, 8 to pass directly from the radiation source assembly 100 to the detector 38. The actual propagation path of the measurement radiation is from the first and the second radiation source 1, 2 in the main propagation direction S through the gas 33 to be measured, and via a reflection from the mirror 43 back through the gas 33 and further through the narrow-band filter 41 to the detector 38. In other respects the structure of the transducer corresponds to the transducer described above, but here the radiation source assembly 100 and the detector 38 are placed in the same transistor casing 60. The advantage of this transducer design is that all active components are located on the same side of the gas 33 to be measured, and thus represent a more compact structure. Further, because the radiation passes back and forth through the gas 33 to be measured, the width L2 of the gas volume can be halved compared to the case of the gas volume width L1 shown in FIG. 9. This could be utilized in pediatric applications, where the gas volumes are small.

Figure 11A:
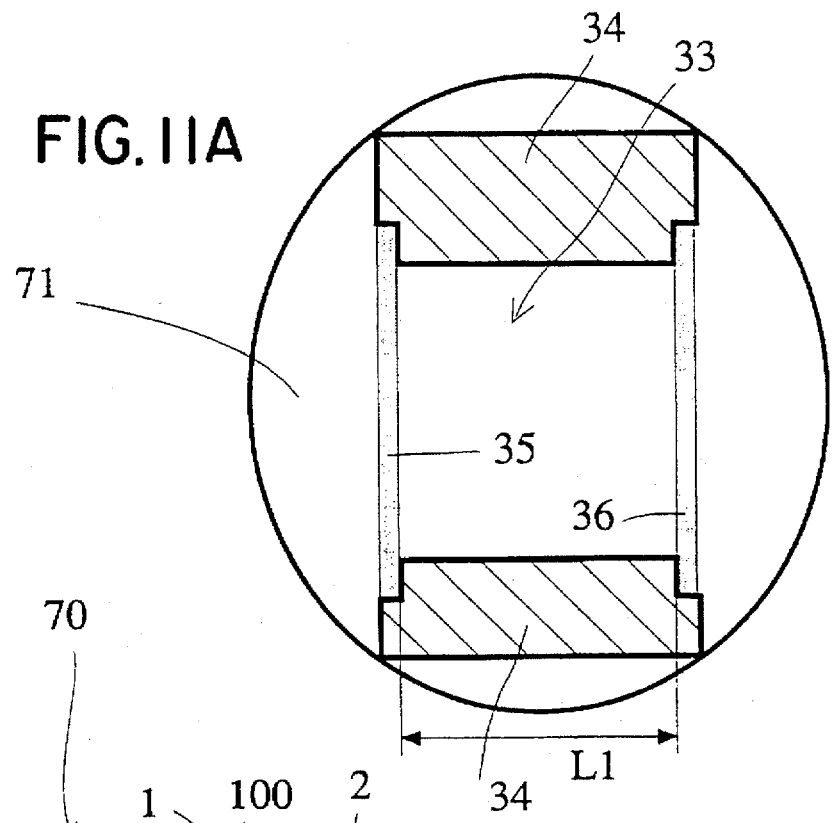
FIG. 11 shows the transducer of FIG. 9 when the sample gas volume is detached.
Figure 11B:
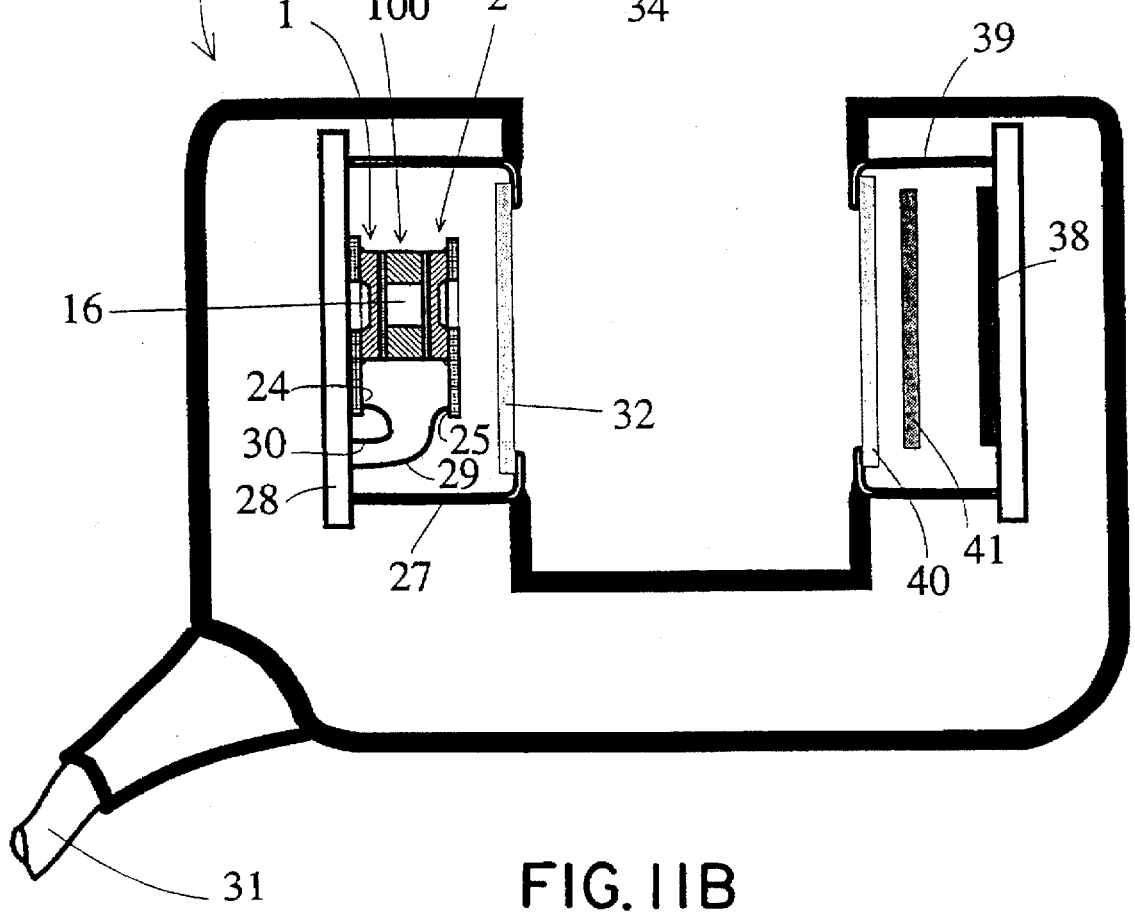

FIG. 11 shows the transducer 70, according to the invention and shown in FIG. 9, when the gas volume 33 is detached. If the transducer is used as a mainstream transducer, then the walls 34 and the windows 35, 36 are parts of the connector 71, which belongs to the patient's breathing circuit, but which can be detached from the circuit. It must be possible to sterilize the connector 71, or it must be disposable, and therefore it is an important characteristic that it can be detached.

Figure 12:
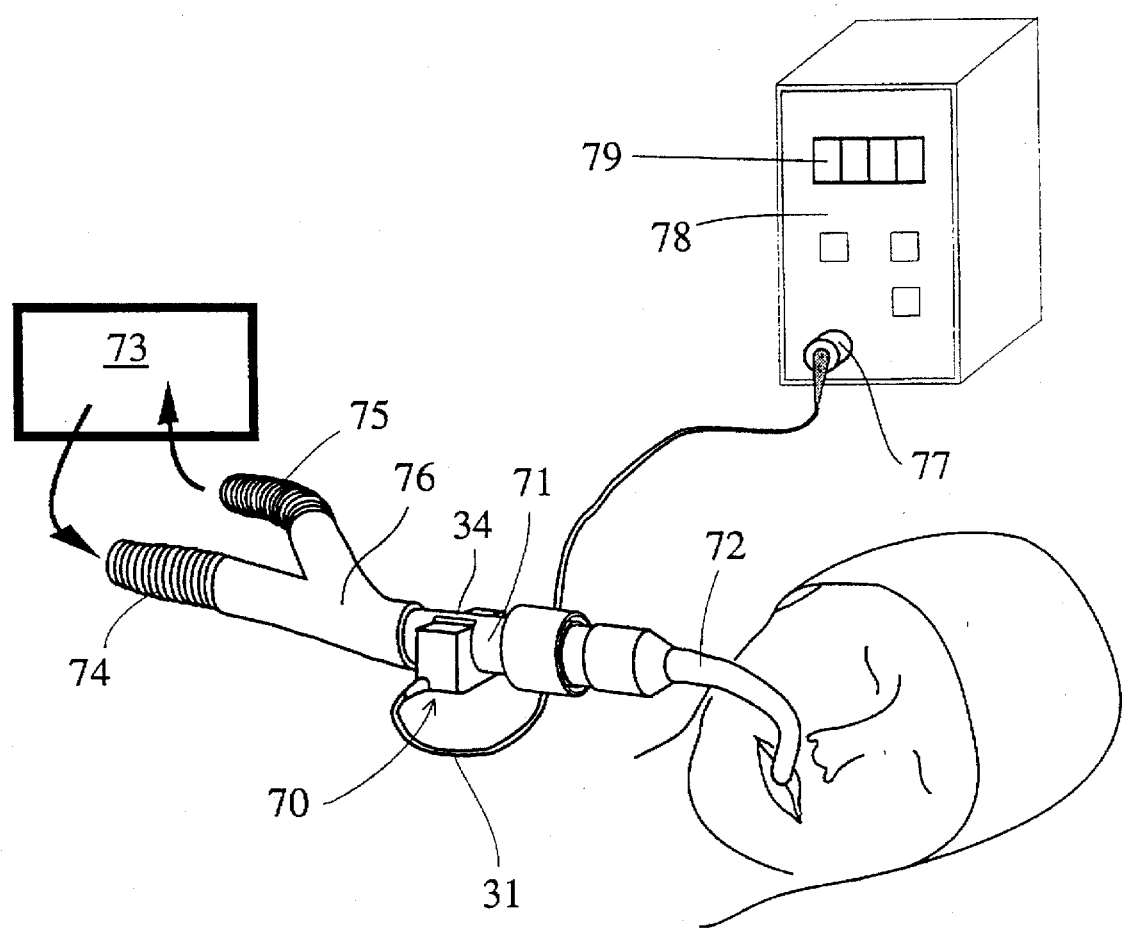
FIG. 12 shows in a plan view the transducer of FIGS. 9 to 11 connected to the breathing circuit of a patient.

FIG. 12 shows a patient's breathing circuit during use, whereby the transducer 70 and the connector 71 are connected between the patient's intubation pipe 72 and the Y piece 76, which connects the input and output hoses 74, 75 of the device 73 maintaining the breathing. The transducer 70 is connected with the connecting line 31 and the connector 77 to the patient monitor 78, where the signal is processed so that the display 79 of the monitor can show the concentration of the gas to be measured as a function of time, i.e. the breathing curve or the concentration values of the inhalation and exhalation.

With the transducers and the radiation source assembly 100 according to the invention it is possible to realize measurements by electrically modulating radiation sources at a sampling frequency, i.e. at a pulse frequency, which is at least about 5 Hz. Typically a speed is achieved, which enables a pulse frequency of at least about 10 Hz. Then the rate of rise of the signal is at most about 50 ms, preferably at most about 20 ms. The operating life of the radiation source assembly is at least thousands of hours, possibly tens of thousand hours.

The above described infra-red analyzer is primarily intended to be used in the mainstream as a carbon dioxide transducer, but using the same principle it would also be possible to measure other gases and media which absorb radiation, such as liquids. In anesthesia it is primarily a question of laughing gas or anesthesia gases. It is quite clear that there are also other gases which can be measured and other applications, in which the infra-red analyzer or the double infra-red source 100 according to the invention could be used.

We claim:

1. A radiation source assembly for optical transducers used for the absorption analysis of a material component present in a medium, whereby the radiation source assembly comprises:

first and second thermal radiation sources, the second radiation source being substantially transparent for radiation emitted by the first radiation source, the first radiation source being located, in relation to the second radiation source, in such a position that the first radiation source emits radiation through the second radiation source;

an absorption band filter located between the first and the second radiation sources, so that the radiation emitted by the first radiation source passes through the filter;

each of said first and second thermal radiation sources comprising; a substrate made of silicon, of a silicon mixture, or of a silicon compound, said substrate having an electrically insulated surface and having at least one recess in the surface; and micro-filaments, which are fastened at their ends to the insulated surface of the substrate to span said recess, the micro-filiaments having radiation emitting regions spaced at a distance from a bottom surface of the recess;

the absorption band of the filter substantially corresponding to the absorption distribution of the material component of the medium to be analyzed by the transducer; and at least the second radiation source in the region of the recess being made of a solid material which is transparent for the radiation used in the radiation source assembly.

2. A radiation source assembly according to claim 1, characterized in that the distance between the microfilaments and the bottom surfaces of the recesses is either approximately equal to the depth of the recesses or smaller than the depth of the recesses; and that the absorption band filter comprises either a filter chamber containing said material component to be analyzed or another medium having an absorption band corresponding as exactly as possible to the absorption band used in the analysis of the material component to be analyzed, or a filter body of solid material, or an interference filter, which prevents the radiation passage as exactly as possible in the same way as the absorption band used in the analysis of the material component to be analyzed.

3. A radiation source assembly according to claim 2, characterized in that both the first and second radiation sources are arranged to emit radiation having a substantially equal wave-length distribution, that the emitting regions of both radiation sources seen in the main propagation direction of the radiation are at least approximately equal, and emission factors of the emitting regions are at least approximately equal at the same frequencies; that the substrates of both radiation sources are transparent for the radiation emitted by said radiation sources; and that the microfilaments spanning the recesses in the substrates in both radiation sources are directed either towards each other, in direction away from each other, or in the same direction, in which the radiation propagated by both radiation sources leaves the radiation source assembly.

4. A radiation source assembly according to claim 2, characterized in that the substrates of both the first and second radiation sources are without any openings, and that the substrates form at least two opposite walls of a filter chamber between the substrates, the walls being transverse to the main propagation direction of the radiation and defining the chamber in the main propagation direction of the radiation.

5. A radiation source assembly according to claim 2, further characterized in that the walls of said filter chamber are made of material transparent for radiation, which walls are hermetically attached to each other in order to form the filter chamber between them.

6. A radiation source assembly according to claim 2, characterized in that said filter chamber is formed by two opposite walls, which are transparent for radiation at least on the wavelength of the radiation emitted by the radiation sources, and which are transverse with respect to the main propagation direction, whereby they define the filter chamber in the main propagation direction of the radiation, said filter chamber being further formed by a peripheral wall, which defines the filter chamber in the direction generally transverse to the radiation, and that the opposite walls and the peripheral wall are hermetically sealed to each other.

7. A radiation source assembly according to claim 2, characterized in that said filter chamber contains that medium, typically gas, which is to be analyzed, and that the concentration of this medium is selected such that the gas absorbs as large a part as possible of the radiation emitted by the first radiation source at the wave-length of the absorption band of that medium, but permits with as small absorption as possible the passage of other wave-lengths, particularly the wave-lengths adjacent said absorption band.

8. A radiation source assembly according to claim 1, characterized in that both the first and second radiation sources are arranged to emit radiation having a substantially equal wave-length distribution, that the emitting regions of both radiation sources seen in a main propagation direction of the radiation are at least approximately equal, and emission factors of the emitting regions are at least approximately equal at the same frequencies; that the substrates of both radiation sources are transparent for the radiation emitted by said radiation sources; and that the microfilaments spanning the recesses in the substrates in both radiation sources are directed either towards each other, in direction away from each other, or in the same direction, in which the radiation propagated by both radiation sources leaves the radiation source assembly.

9. A radiation source assembly according to claim 8, characterized in that at least those regions of the substrates through which the radiations emitted by the first and second radiation source propagate in the main propagation direction, are coated with a film decreasing reflections at the wave-length hand of the radiation.

10. A radiation source assembly according to claim 1, characterized in that the substrates of both the first and second radiation sources are without any openings, and that the substrates form at least two opposite walls of a filter chamber between the substrates, the walls being transverse to the main propagation direction of the radiation and defining the chamber in the main propagation direction of the radiation.

11. A radiation source assembly according to claim 10, wherein one or both of said substrates are formed to provide peripheral walls defining said filter chamber transverse to the main propagation direction of the radiation, and the substrates of the radiation sources are hermetically attached to each other in order to form the filter chamber between them.

12. A radiation source assembly according to claim 10, further characterized in that an insert is placed between said substrates, said insert having a walls defining said filter chamber in the direction transverse to the main propagation direction, said insert being of other material than the substrate material and being hermetically attached to the substrates of both radiation sources in order to for the filter chamber between them.

13. A radiation source assembly according to claim 10, further characterized in that the walls of said filter chamber are made of material transparent for radiation.

14. A radiation source assembly accordingly to claim 1, characterized in that the micro-filaments are generally straight, film-like elements lying in the plane of the upper surfaces of the substrates or at most at a distance from them which corresponds to the thickness of a substrate insulation layer and/or the micro-filaments, that the material of the filaments is formed in or on the surfaces of the substrates by vaporizing, sputtering, or printing, and by then etching said recesses in the substrates, and that the volume of a single micro-filament is at most about 200,000 $\mu m^3$, preferably at most about 50,000 $\mu m^3$, and typically of the order 2,000 to 20,000 $\mu m^3$, whereby the thermal time constant of the micro-filament is at most about 50 ms, preferably at most about 10 ms, and typically of the order 0.5 to 5 ms.

15. A radiation source assembly according to claim 14, characterized in that in other regions except in the regions of the recesses, the substrates are coated with silicon nitride, silicon carbide, metal oxide, or other electrically isolating material film protecting the substrate against the etching, and that the micro-filaments are also protected by silicon nitride, silicon carbide, metal oxide, or other electrically isolating material film protecting them against the etching and/or oxidizing.

16. A radiation source assembly according to claim 15, characterized in that in the first radiation source, a bottom surface of the recess or a back surface of the substrate is coated to become reflective for the radiation emitted by the first radiation source, the micro-filaments of the first radiation source being directed toward the second radiation source as seen from the bottom surface of the recess, or the radiation source assembly comprises a separate mirror on a side of the first radiation source, which is directed away from the second radiation source.

17. A radiation source assembly according to claim 1, characterized in that at least those regions of the substrates through which the radiations emitted by the first and second radiation sources propagate in the main propagation direction, are coated with a film decreasing reflections at the wave-length band of the radiation.

18. A radiation source assembly according to claim 1, characterized in that the transparency of the second radiation source is obtained by using as the substrate material silicon, a silicon mixture or a silicon compound transparent for the radiation, or by forming the recess to extend through the substrate and by attaching on the substrate at a distance from the micro-filaments, such as silicon, a silicon mixture, a silicon compound, sapphire, glass, quartz, calcium fluoride, or silicon nitride, which is transparent for the radiation emitted by the first radiation source.

19. An optical transducer for observing and/or measuring the concentration of a material component to be analyzed present in a medium, the transducer comprising:

a radiation source assembly having first and second thermal radiation sources, the second radiation source being substantially transparent for radiation emitted by the first radiation source, the first radiation source being located in relation to the second radiation source, in such a position that the first radiation source emits radiation through the second radiation source; an absorption band filter located between the first and the second radiation sources, so that the radiation emitted by the first radiation source passes through the filter; and a radiation detector located to receive the radiation emitted by the first and second radiation sources, the radiation source assembly and the radiation detector forming a transducer unit, in which the radiation source assembly is spaced from the radiation detector by a given distance in the propagation direction of the radiation, whereby a measurement chamber containing the material component to be analyzed can be placed in the space between the radiation source assembly and the radiation detector, the absorption band of the absorption band filter substantially corresponding to the absorption distribution of the material component in the medium to be analyzed with the transducer; and each of said first and second thermal radiation sources of the radiation source assembly comprising a substrate having a recess and micro-filaments, which are fastened at their ends to a surface of the substrate to span said recess said micro-filaments having a radiation emitting region spaced at a distance from a bottom surface of the recess, whereby the transducer's electrical sampling frequency is at least about 5 Hz, preferably at least about 10 Hz, the rise time of a signal being at most about 50 preferably at most about 20 ms.

20. A transducer according to claim 19, characterized in that the radiation source assembly and the radiation detector in the transducer are located adjacently in a direction transverse to the main propagation direction of the radiation.

21. A transducer according to claim 20, characterized in that the transducer further comprises a mirror, which is located at a distance from the radiation source assembly and the radiation detector, the plane of the mirror being approximately perpendicular to the main propagation direction of the radiation, the reflection of the radiation by the mirror increasing the optical distance between the radiation source assembly and the radiation detector.

22. A transducer according to claim 19, characterized in that the radiation source assembly and the radiation detector are located opposite each other in the transducer and spaced at a distance from each other in the propagation direction of the radiation.

23. A transducer according to claim 19, characterized in that it further comprises an additional filter in front of the radiation detector seen in the input direction of the radiation, and that this additional filter is a band-pass filter having a pass-band width, which is slightly larger than the width of the absorption band of the medium to be analyzed.

24. A transducer according to claim 19, characterized in that said absoprtion band filter comprises a filter chamber containing said material component to be analyzed or an other medium having an absorption band corresponding as exactly as possible to the absorption band used in the analysis of the material component to be analyzed, or a filter body of solid material, or an interference filter, which prevents the radiation passage as exactly as possible in the same way as the absorption band used in the analysis of the material component to be analyzed.

* * * * *